(12) United States Patent
Popovic et al.

(10) Patent No.: US 9,173,582 B2
(45) Date of Patent: Nov. 3, 2015

(54) ADAPTIVE PERFORMANCE TRAINER

(75) Inventors: Djordje Popovic, Oceanside, CA (US); Gene Davis, Oceanside, CA (US); Chris Berka, Carlsbad, CA (US); Adrienne Behneman, Carlsbad, CA (US); Giby Raphael, Carlsbad, CA (US)

(73) Assignee: ADVANCED BRAIN MONITORING, INC., Carlsbad, GA (US)

( * ) Notice: Subject to any disclaimer, the term of this patent is extended or adjusted under 35 U.S.C. 154(b) by 570 days.

(21) Appl. No.: 12/766,322

(22) Filed: Apr. 23, 2010

(65) Prior Publication Data
US 2011/0105859 A1 May 5, 2011

Related U.S. Application Data

(60) Provisional application No. 61/172,613, filed on Apr. 24, 2009.

(51) Int. Cl.
*A61B 5/00* (2006.01)
*A61B 5/04* (2006.01)
(Continued)

(52) U.S. Cl.
CPC .......... *A61B 5/0402* (2013.01); *A61B 5/02405* (2013.01); *A61B 5/486* (2013.01);
(Continued)

(58) Field of Classification Search
CPC ............... A61B 5/048; A61B 5/0476–5/0484; A61B 5/7207–5/7267; A61B 5/16–5/168; A61B 5/18; A61B 5/11; A61B 5/0402; A61B 5/0488; A61M 21/00; A61M 21/0094; A61M 21/02; G06F 3/016; G06F 3/038; G06F 3/04812–3/04886; A63B 2220/16–2220/35; A63B 2220/53; A63B 2220/62; A63B 2220/803–2220/805; G08B 21/0423; G08B 21/0446; G09B 19/0038
See application file for complete search history.

(56) References Cited

U.S. PATENT DOCUMENTS

| 4,617,525 A | 10/1986 | Lloyd |
| 4,802,485 A | 2/1989 | Bowers et al. |

(Continued)

FOREIGN PATENT DOCUMENTS

| JP | 7-36362 | 2/1995 |
| JP | 2004-073386 A | 3/2004 |

(Continued)

OTHER PUBLICATIONS

International Search Report and Written Opinion issued in PCT/US2010/032291, Dec. 6, 2010, 10 pages.
(Continued)

*Primary Examiner* — William Thomson
*Assistant Examiner* — Shirley Jian
(74) *Attorney, Agent, or Firm* — Procopio, Cory, Hargreaves & Savitch LLP (57) ABSTRACT

Techniques for accelerating training through optimization of the psychophysiological state of the trainee are provided. These techniques include an adaptive performance training system configured to acquire, analyzed, display, and translate data that reflects the psychophysiological state of the user, including the electrical activity of the brain (EEG), the heart (EKG), the musculature (EMG), respiration and other parameters that characterize the state of the user in real-time. The system includes a plurality of feedback mechanisms for providing visual, auditory, and/or tactile feedback based on the current psychophysiological state of the user and for facilitating moving the user toward a goal psychophysiological state for performing a particular task and for optimizing performance of that task.

32 Claims, 3 Drawing Sheets

(51) Int. Cl.
    *A61B 5/0402*           (2006.01)
    *A61B 5/024*            (2006.01)
    *A61B 5/021*            (2006.01)
    *A61B 5/0476*           (2006.01)
    *A61B 5/0488*           (2006.01)
    *A61B 5/08*             (2006.01)
    *A61B 5/11*             (2006.01)
    *A61B 5/16*             (2006.01)

(52) U.S. Cl.
    CPC .............. *A61B 5/021* (2013.01); *A61B 5/0476* (2013.01); *A61B 5/0488* (2013.01); *A61B 5/0816* (2013.01); *A61B 5/11* (2013.01); *A61B 5/16* (2013.01)

(56) References Cited

U.S. PATENT DOCUMENTS

| | | | | |
|---|---|---|---|---|
| 4,949,726 | A * | 8/1990 | Hartzell et al. | 600/544 |
| 4,984,578 | A | 1/1991 | Keppel et al. | |
| 5,435,317 | A | 7/1995 | McMahon et al. | |
| 5,447,166 | A * | 9/1995 | Gevins | 600/544 |
| 5,458,105 | A | 10/1995 | Taylor et al. | |
| 5,477,867 | A | 12/1995 | Balkanyi | |
| 5,671,733 | A | 9/1997 | Raviv et al. | |
| 5,724,987 | A * | 3/1998 | Gevins et al. | 600/544 |
| 6,045,514 | A | 4/2000 | Raviv et al. | |
| 6,057,767 | A | 5/2000 | Barnoach | |
| 6,093,158 | A | 7/2000 | Morris | |
| 6,371,120 | B1 | 4/2002 | Chiu et al. | |
| 6,607,484 | B2 * | 8/2003 | Suzuki et al. | 600/300 |
| 6,744,370 | B1 * | 6/2004 | Sleichter et al. | 340/576 |
| 6,959,259 | B2 * | 10/2005 | Vock et al. | 702/142 |
| 7,171,331 | B2 * | 1/2007 | Vock et al. | 702/160 |
| 7,202,851 | B2 * | 4/2007 | Cunningham et al. | 345/156 |
| 7,248,915 | B2 | 7/2007 | Rönnholm | |
| 7,403,814 | B2 * | 7/2008 | Cox et al. | 600/544 |
| 7,602,301 | B1 * | 10/2009 | Stirling et al. | 340/573.1 |
| 7,716,988 | B2 | 5/2010 | Ariav et al. | |
| 7,819,217 | B2 * | 10/2010 | Ishikawa et al. | 180/272 |
| 7,821,407 | B2 * | 10/2010 | Shears et al. | 340/573.1 |
| 7,825,815 | B2 * | 11/2010 | Shears et al. | 340/573.1 |
| 7,868,757 | B2 | 1/2011 | Radivojevic et al. | |
| 7,978,081 | B2 * | 7/2011 | Shears et al. | 340/573.1 |
| 8,033,996 | B2 * | 10/2011 | Behar | 600/300 |
| 8,340,752 | B2 * | 12/2012 | Cox et al. | 600/544 |
| 8,519,835 | B2 * | 8/2013 | Dunko | 340/407.1 |
| 8,532,756 | B2 * | 9/2013 | Schalk et al. | 600/544 |
| 8,790,255 | B2 * | 7/2014 | Behar | 600/300 |
| 2003/0199945 | A1 | 10/2003 | Ciulla | |
| 2004/0152995 | A1 * | 8/2004 | Cox et al. | 600/544 |
| 2006/0057549 | A1 | 3/2006 | Prinzel, III et al. | |
| 2006/0212273 | A1 | 9/2006 | Krausman et al. | |
| 2007/0050715 | A1 * | 3/2007 | Behar | 715/706 |
| 2007/0219059 | A1 * | 9/2007 | Schwartz et al. | 482/8 |
| 2007/0273611 | A1 | 11/2007 | Torch | 345/8 |
| 2008/0208015 | A1 * | 8/2008 | Morris et al. | 600/301 |
| 2008/0214903 | A1 | 9/2008 | Orbach | |
| 2008/0308112 | A1 | 12/2008 | Aarts | |
| 2009/0047645 | A1 | 2/2009 | Dibenedetto et al. | |
| 2009/0051544 | A1 * | 2/2009 | Niknejad | 340/573.1 |
| 2009/0069707 | A1 * | 3/2009 | Sandford | 600/545 |
| 2009/0075781 | A1 | 3/2009 | Schwarzberg et al. | |
| 2009/0099471 | A1 | 4/2009 | Broadley et al. | |
| 2009/0156954 | A1 * | 6/2009 | Cox et al. | 600/544 |
| 2010/0049073 | A1 | 2/2010 | Bader | |
| 2010/0063778 | A1 * | 3/2010 | Schrock et al. | 702/188 |
| 2010/0094154 | A1 * | 4/2010 | Schalk et al. | 600/544 |
| 2010/0131028 | A1 | 5/2010 | Hsu et al. | |
| 2010/0283618 | A1 | 11/2010 | Wolfe et al. | |
| 2010/0318007 | A1 | 12/2010 | O'Brien | |
| 2012/0071771 | A1 * | 3/2012 | Behar | 600/508 |
| 2012/0223823 | A1 * | 9/2012 | Dunko | 340/407.1 |

FOREIGN PATENT DOCUMENTS

| | | |
|---|---|---|
| JP | 2005-526529 A | 9/2005 |
| JP | 2008-532587 A | 8/2008 |
| JP | 2011-517962 A | 6/2011 |

OTHER PUBLICATIONS

Extended European Search Report for related EP Patent Application No. EP10767858.3, dated May 7, 2013, in 6 pages.

Office Action dated Feb. 18, 2014 for related JP Patent Application No. 2012-507445 in 5 pages.

* cited by examiner

ADAPTIVE PERFORMANCE TRAINER

RELATED APPLICATION

This application claims the benefit of U.S. provisional patent application Ser. No. 61/172,613 entitled "ADAPTIVE PERFORMANCE TRAINER," filed on Apr. 24, 2009, which is incorporated herein by reference in its entirety.

GOVERNMENT LICENSE RIGHTS

This invention was made with government support under contract #NBCHC090054/C09PC75596 awarded by Defense Advanced Research Projects Agency (DARPA). The government has certain rights in the invention.

FIELD OF THE INVENTION

The present invention generally relates to using psychophysiological feedback for accelerating learning and more specifically to systems and methods for accelerating learning using multi-sensory feedback to make a user aware of their mental state and train them to interactively maintain or vary their mental state or to move into a state that is known to be beneficial for a particular task or activity.

BACKGROUND

There are numerous methods available for detecting physiological signals including electroencephalograph (EEG), electrocardiograph (EKG), and electromyography (EMG) and for translating these signals into meaningful feedback to provide information to the user regarding their psychophysiological state. This is most frequently done in a controlled laboratory environment involving multiple computers and trained technical staff. In addition, the majority of the applications described involve training the user to increase or decrease simple derivative measures of EEG such as the alpha or theta bands or increasing or decreasing heart rate or a specific pattern of muscle activity.

It is theorized that each of the major sub-bands of biofeedback EEG (delta, theta, alpha, beta) correspond with unique subjective characteristics of an individual. The delta band is observed most clearly in deep sleep, the theta band in light sleep and drowsiness, the alpha band in a variety of wakeful states involving creativity, calm and inner awareness, and the beta band in alert wakeful situations with external focus. One problem with laboratory based feedback training is that it is conducted in a constrained environment with relatively limited number of stimuli, situations or tasks that the subject is supposed to learn how to handle. Specifically, training is typically confounded with few distracters that tend to be perceived as artificial and become predictable after some time spent in the lab. In effect, the knowledge gained or skills learned may not transfer well to real-world applications and the retention times are short. Repeated visits to the laboratory are then required for the user to maintain the control over physiological states.

Many different approaches have been taken to EEG biofeedback to achieve mental state control. For example, U.S. Pat. No. 4,928,704 describes a biofeedback method and system for training a person to develop useful degrees of voluntary control of EEG activity. EEG sensors are attached to cortical sites on the head for sensing EEG signals in a controlled environmental chamber. The signals are amplified and filtered in accordance with strict criteria for processing within time constraints matching natural neurological activity. The signals are filtered in the pre-defined bands of alpha, theta, beta and delta, and fed back to the monitored person in the form of optical, aural or tactile stimuli. In another example, U.S. Pat. No. 4,949,726, U.S. Pat. No. 5,024,235, and U.S. Pat. No. 5,406,957 describe an EEG Neurofeedback apparatus for training and tracking of cognitive states which measures bioelectric signals in bandwidth windows to produce a composite amplitude by a fast Fourier transform on an amplified signal. Selected bandwidths are displayed and monitored by computer to enable training of a person being monitored with audio or verbal feedback. All these systems are lab-based, and cannot be applied in the field. In addition, the definition of desired or target mental states is given 'ad hoc' without any reference to mental states of subjects who are considered experts in a task at hand.

SUMMARY

Systems and methods for adaptive performance training are provided. According to an aspect of the present invention, a portable, field deployable system is provided that allows users to train in real-world settings rather than a laboratory. Aspects of the present invention use psychophysiological assessments in combination with targeted feedback to accelerate skill acquisition and provide quantitative evidence of successful training by detecting, in real-time, cognitive and physiological states of the trainee under various conditions. Embodiments provide a portable, reliable, and easy-to-use feedback system that can be applied in multiple environments such as an office, at home or in field operations. Embodiments include multiple interfaces and outputs to automatically shape the mental state of the user towards a pre-selected "goal state" by progressively providing visual, auditory or haptic (tactile) feedback on state changes and progression toward the goal mental state. By individualizing and automating training, the provided techniques accelerate instruction and improves performance.

According to an embodiment, a system for accelerating learning of a task using real-time data acquisition and analysis of real-time psychophysiological signals obtained from a user is provided. The system includes a monitoring module configured to continuously monitor psychophysiological signal data collected from a plurality of sensors attached to a user while the user is performing the task to be learned. The system also includes an expertise profiler module configured to analyze the psychophysiological signal data to generate a current psychophysiological state of the user, to compare the current psychophysiological state of the user to one or more goal states associated with expert performance of the task to be learned, and to generate a set of control signals based on difference between the current psychophysiological state of the user to one or more goal states. The system also includes a real-time feedback generator configured to receive the control signals from the expertise profiler module, and to deliver multimodality feedback to the user in real-time to guide the user toward the one or more goal states, wherein the multimodality feedback delivered to the user is based on the control signals received from the expertise profiler module.

According to another embodiment, a method for accelerating learning of a task using real-time data acquisition and analysis of real-time psychophysiological signals obtained from a user using an adaptive portable training device worn by the user is provided. The method includes continuously monitoring at the portable training device psychophysiological signal data from a plurality of sensors attached to a user while the user is performing the task to be learned, analyzing at the portable training device the psychophysiological signal data to generate a current psychophysiological state of the user, comparing at the portable training device the current psychophysiological state to one or more goal states associated with expert performance of the task to be learned, determining at the portable training device multimodality feedback to be provide to the user based on the comparison of the current psychophysiological state of the user to the one or more goal states, and delivering from the portable training device the multimodality feedback to the user in real-time to guide the user toward the one or more goal states, wherein the multimodality feedback delivered to the user is based on the control signals received from the expertise profiler module.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Systems and methods to accelerate learning are provided. These techniques can be used to facilitate a user's progression from novice to expert for a selected task by using automated inferences from neurological and psychophysiological measurements and multi-sensory feedback to make the user aware of his or her mental state and to assist the user in shifting to a mental state that is known to be beneficial for a particular task or activity. After reading this description, it will become apparent to one skilled in the art how to implement the invention in various alternative embodiments and alternative applications. Although various embodiments of the present invention are described herein, it is understood that these embodiments are presented by way of example only, and not limitation. As such, this detailed description of various alternative embodiments should not be construed to limit the scope or breadth of the present invention. The systems and methods disclosed herein can accelerate the learning of a novice and assist in the transition from a novice to expert level faster than conventional learning techniques.

Embodiments of the techniques disclosed herein can use model goal states identified as characteristic of expertise at a particular task in order to shape the mental state of the user, improve performance of the user at the task, and facilitate accelerated training in the task. Conventional neuro-feedback systems have relied on the rudimentary definitions of mental states associated with the major sub-bands of EEG (delta, theta, alpha, and beta). The techniques provided herein provide the user with a much more sophisticated and targeted approach to training where neurological and psychophysiological metrics that are associated with a levels of skill in a task that progress from a novice level to an expert level are used to steer the user to a set of one or more goal psychophysiological states.

Recent investigations suggest that changes in EEG power spectra and event-related EEG can be identified as associated with stages of skill acquisition in both simple and complex tasks. Relationships between EEG parameters and proficiency in real world activities have been reported in various activities, such as golf putting, archery, and marksmanship. In these real-world task environments, the most predictive data is acquired during the period of mental preparation (usually between 8-15 seconds in duration) before the skilled movements occur, referred to in sports medicine as the "pre-shot routine." The pre-shot routine is characterized by a progressive increase of the power of EEG in the alpha bands (8-12 Hz), particularly over the parietal-occipital regions, with decreased activation in cortical regions not relevant to skilled visuomotor tasks. The pre-shot period is also characterized by heart rate deceleration and a decrease in electrodermal skin conductance levels. Heart rate changes are also believed to reflect the focusing of attention and the skill-related aspects of sensory-motor preparation for performance. Consistency and reproducibility of the successful pre-shot routine is a major feature that distinguished novice from expert. The techniques used herein can monitor the psychophysiological state of the user and generate feedback that can help to steer the user to a psychophysiological state that is associated with expertise in a particular task.

Figure 1:
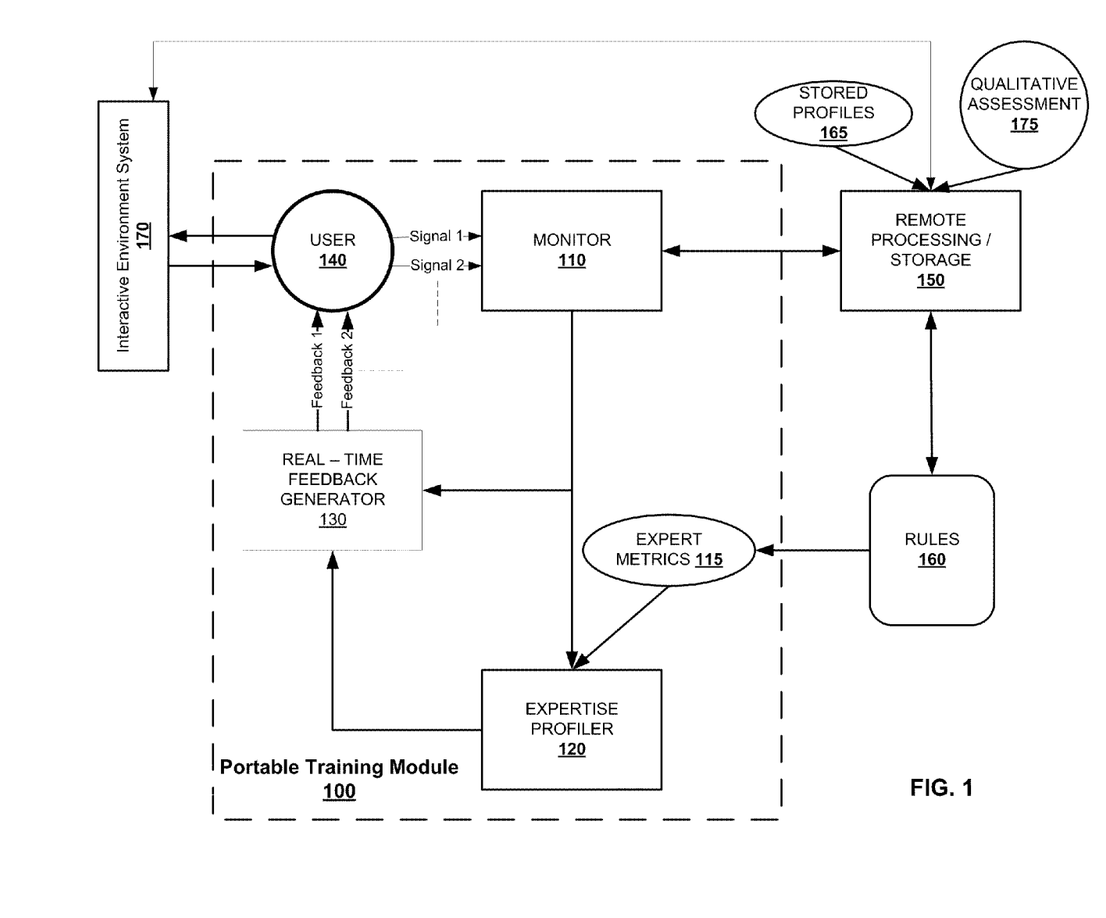
FIG. 1 is a block diagram is a block diagram of the functional components of a system for accelerated skill learning according to an embodiment.

FIG. 1 is a block diagram is a block diagram of the functional components of a system for accelerated skill learning according to an embodiment. FIG. 1 illustrates the relationships between the functional components of the system and the flow of data between components. Quantitative metrics that are well-defined for expert performance can be extracted from the physiological characteristics of the user, and the transition from novice-to-expert can be facilitated by providing continuous real-time feedback of the changes in these metrics during stages of learning.

The system includes a portable training module 100 that can be worn by a user 140. The portable training module 100 includes a monitor module 110, an expert metrics data store 115, and a real-time feedback generator module 130. The monitoring module interacts with a remote storage and processing module 150, a rules module 150, and an interactive environment system 170. A detailed description of each of the modules and the interaction between the modules is provided below.

Monitor module 110 can be configured to receive signal data from various types of sensors that are configured to collect psychophysiological signals from user 140. These signals can include, but are not limited to, electroencephalogram (EEG), electrocardiogram (EKG) electrooculogram (EOG), electromyogram (EMG), respiration, heart rate, body movement, galvanic skin reaction, blood pressure, blood flow, blood chemistry, behavioral responses, or any other physiological signals that change as a function of neurocognitive or emotional state, or some combination thereof. This signal data can be analyzed to determine a current state of the user. For example, the intensity, quality and frequency of eye movements change as a function of the level of alertness/drowsiness. Intense and rapid scanning eye movements, typical for active wakefulness, become less frequent and the ocular activity in general gradually decreases as the subject becomes fatigued/drowsy, until a different type of regular, sinusoidal eye movements, the so called Slow Eye Movements (SEM), occur indicating the onset of the initial stage of sleep. The impeding drowsiness leads to a notable decrease in the volume of respiration as compared with the preceding state of active wakefulness, and sometimes to slow sinusoidal variations (with a period of 90-120 seconds) in peak-to-peak amplitudes of breaths. In another example, irregular respiration can be a sign of arousal, anxiety, or other strong emotions.

Galvanic skin reaction (GSR), EMG of selected muscle groups (e.g. neck, facial musculature, forearm and/or hand), size of the pupil and facial expression (both captured with e.g. a small camera), and heart rate measured with a pulse oximeter are commonly used to make inferences about emotional state of users of computers/computer systems. Task-related variations in oxygenation and/or blood flow through different parts of the brain are commonly used, especially in functional magnetic resonance imaging (fMRI) studies, to identify brain regions involved in or crucial for the execution of the studied task. Those skilled in the art will recognize that any number physiological signals that change as a function of a cognitive or emotional state can be collected from the user 140, and any number of corresponding sensors can be used for this purpose and that the sensors can be used in various embodiments.

Monitor module 110 also comprises algorithms for basic signal conditioning. For example, monitor 110 can include algorithms for basic signal conditions, such as artifact recognition and rejection, band-pass filtering, other signal conditioning algorithms, or a combination thereof.

Expertise profiler module 120 is configured to receive physiological signal data collected by monitor 110. The signal data received from monitor can be conditioned by monitor module 110 before being provided to the expertise profiler module 120. According to an embodiment, the expertise profiler module 120 can be configured to extract quantitative metrics corresponding to the different stages of skill acquisition from the signal data collected by monitor module 110 and to compare the extracted metrics to pre-defined indices from an expert metrics data store 115. The expert metrics data store 115 can include various metrics common to expert performance of a task that a user of the system is to learn or is in the process of learning and can include one or more goal states that represent a desired psychophysiological state that are typically present in expert level performance of the task. The metrics may include, but are not limited to EEG signatures of attention, workload, learning and memory, heart-rate variability analysis, stress and anxiety levels, measures of sympathetic and parasympathetic activation, frequency and timing of eye blinks, completion time of trials and trial-to-trial variability across measures.

According to an embodiment, the expert metrics data can include power spectral density (PSD) data of the subject's EEG activity recorded from multiple scalp sites, computed on a second-by-second basis for the range of frequencies from 1 to 50 Hz in 1 Hz steps. According to an embodiment, power can be computed using standard non-parametric algorithms (Fast Fourier Transform, filter banks, and so forth) or parametric techniques such as auto-regressive (AR) models or autoregressive moving-average (ARMA) models. The computed PSD indices can be further be grouped or summed into the conventional EEG bands known from the literature, namely delta (1-4 Hz), theta (4-7 Hz), alpha (8-13 Hz), beta (13-30 Hz) and gamma (30-50 Hz). According to an embodiment, specific changes in PSD of the EEG across different scalp sites can serve as measures of alertness, mental effort and engagement, workload imposed on the subject by a task, and the subject's working memory.

According to an embodiment, the expert metrics data can include data representing peak times (latencies), peak amplitudes and wave shapes of the subject's event-related potentials (ERPs) elicited by the task stimuli. For example, ERPs are measured brain responses that are the result of thought or perception. In other words, the ERPs are electrophysical responses to internal or external stimulus. Data related to various ERPs can be included in the expert metrics data store 115 including N100 which is elicited by any unpredictable stimulus in the absence of task demands, N100 and P200 have been associated with the latter attentive stages of information processing, P300 which is an ERP elicited by infrequent task-related stimuli, N400 which is typically elicited by meaningful or potentially meaningful inputs, the late Memory-Related Late Positive Component, and other event-related potentials, or a combination thereof. According to an embodiment, these potentials can be timed to the times of occurrence of known stimuli in the tests/tasks presented to the subject (stimulus-related ERPs), or to the times of occurrence of the subject's behavioral responses to the presented task/test, such as a button press (response-related ERPs), or to a physiological event such as eye gaze fixation (Fixation-Locked ERPs, or FLERPs) that can be tracked by an optical eye tracker with a camera, or by means of EOG. Experimental literature has convincingly demonstrated that latencies, amplitudes and overall shape of event-related potentials is affected by, and can therefore reflect, perceptual acuity and speed, decision-making speed and accuracy, capacity for selective, focused and global attention, or situational awareness. According to an embodiment, the PSD computations described above can be combined with ERPs (whether stimulus- or response-related, or FLERPs) into power event-related potentials (PERPs), which are the PSD computed as described above on a segment of EEG that contains ERP(s) centered to either a stimulus, or response or a physiological event such as eye fixation, or a heartbeat.

According to an embodiment, the expert metrics data can include instantaneous heart rate data. Instantaneous heart rate data can be computed from the time interval between two successive QRS complexes in the recorded EKG, and the heart rate variability (HRV) signal, can be computed as the first difference of the instantaneous heart rate.

According to an embodiment, the expert metrics data can include the power of the HRV signal in two ranges, the low frequency (LF) range from 0.04 to 0.15 Hz and high frequency (HF) range from 0.15 to 0.4 Hz. Power can be computed using standard non-parametric algorithms, such as Fast Fourier Transform, filter banks, or other techniques, or parametric techniques such as auto-regressive (AR) models or autoregressive moving-average (ARMA) models. According to an embodiment, once the LF and HF power is computed, the LF and HF power can be presented as percentages of the total power, or a ratio of the LF to HF power can be computed. The LF power and the LF/HF ratio have been shown to be related to the degree of sympathetic stimulation, whereas the HF power reflects the degree of parasympathetic stimulation. Therefore, these measures can indicate emotional states associated with an autonomic arousal, such as anxiety, anger or fear.

According to an embodiment, the expert metrics data can include EOG/EEG data. If EOG or frontal or prefrontal EEG is recorded for a user, the subject's EOG or (pre)ontal delta power associated with slow horizontal eye movements. As described above, slow horizontal eye movements (SEM) are indicative of a transition from wakefulness to initial stage of sleep, and can therefore be used as one of the measures or indicators of drowsiness/alertness.

According to an embodiment, the expert metrics data can include variance data of band-pass filtered EMG signal, if EMG is recorded. According to an embodiment, EMG does not have to be recorded with a special sensor/channel, since some amount of EMG from the facial and jawing muscles will be present in the EEG acquired from the scalp. High EMG activity is associated with active wakefulness, high mental engagement, or states of anxiety, fear, impatience, or anger. Therefore, according to an embodiment, EMG can be used in assessment of alertness, mental effort, workload, and emotional states.

According to an embodiment, the expert metrics data can include engagement metrics. In some embodiments, the engagement metrics can be derived using the methods disclosed in U.S. Pat. Nos. 6,496,724 and 6,625,485 which are incorporated herein by reference in their entirety. These methods for determining engagement metrics rely on the acquisition of three baseline conditions and the prediction of a fourth mental state to determine the subject's alertness, mental effort and engagement during each of the sub-tasks by measuring on a second-by-second basis the power of the EEG recorded from multiple scalp locations at frequencies from 1 to 40 Hz in 1 Hz steps, and using a four-class quadratic discriminant function to convert these power measures into probabilities that the subject's level of mental effort and engagement belongs to one of the four classes defined as High Engagement, Low Engagement, Distraction and Drowsiness.

According to an embodiment, the expert metrics data can include mental workload metrics. According to an embodiment, mental workload metrics can be characterized using a two-class discriminant function to convert these power measures into probabilities that the subject is at Low or High workload.

Real-time feedback generator module 130 can be configured to provide real-time feedback to the user to help to make the user aware of his or her mental state or move into a target mental state. According to an embodiment, feedbacks that can be collected without the need for extensive processing or summarizing can be collected directly from the monitoring module 110. For example, the monitoring module 110 can provide signal data representing body movement, respiration, heart rate, and/or other physiological signal data.

According to an embodiment, expertise profiler module 120 can also include algorithms that generate a control signal inputs to the real-time feedback generator module 130. The signals generated and output by the expertise profile module 120 to be used as inputs to the real-time feedback generator module 130 can be based on the results of the expertise profile module 120 comparing the input signals from the monitor module 110 with the desired metrics from the expert metrics data store 115.

According to an embodiment, different feedback modalities can be used, which can include, but are not limited to, audio, visual, haptics vibrators, smell, heat or cold or other feedback techniques that provide feedback with minimal interference to the task performed and also requires minimal cognitive load. According to an embodiment, the feedbacks can include proportional indications of the amplitude and/or frequency of the processed parameter derived from past or predictive performance, or in some embodiments, the feedback can include simple commands to guide the user to the desired state. The feedback provided can help to steer the user toward one or more goal states associated with a training profile. The type of feedback provided can be determined in part based on the type of training in which the user is participating.

The portable training module 100 is completely portable, and hence, can be deployed in the field with minimal interference to the task performed. Various types of wearable sensors are available for the acquisition of EEG, EOG, EMG, EKG, respiration, GSR, blood pressure, near-infrared brain or muscle spectroscopy (NIRS). These and other types of sensors can be used with the portable training module 100.

According to an embodiment, the EEG data can be acquired using the wireless, wearable, and field-deployable EEG apparatus disclosed in U.S. Pat. No. 6,640,122, which is incorporated herein by reference as if it were set forth in its entirety.

According to an embodiment, the portable training module 100 can be used for indoor training as well as a research platform to collect data and to derive metrics that can be used to characterize expertise in a particular task. The derived metrics can be used to populate expert metrics data store 115.

In some embodiments, the signals output by the monitor module 110 can be output to a remote computer system (not shown) for offline analysis and storage. In some embodiments, the signals output by monitor module 110 can be wirelessly transmitted to a remote personal computer system or laptop to collect the signals for offline analysis. A remote processing and storage module 150 can be implemented on the remote computer system. The remote computer system can include additional software for processing the data collected from the portable training module 100 and for generating performance reports that assess the user's performance of a particular task, training reports that can suggest additional steps for improving and accelerating the user's mastery of the task, or both.

Interactive environment system 170 provides an environment in which the user can learn a task. The interactive environment system 170 can be used to educate a user prior to performing the task or tasks to be learned, to provide real-time feedback to the user throughout the learning process, or both. The interactive environment system 170 can include systems for monitoring additional parameters of task performance, including but not limited to neurophysiological, neuropsychological, behavioral and subjective measures of alertness, attention, learning and memory. According to an embodiment, the interactive environment system 170 can also include systems for monitoring various types of user interactions with various interfaces, including but not limited to, key presses, mouse clicks, a degree of pressure on a joysticks or other types of pressure-sensitive equipment or computer interface, or a combination thereof. These interactions can be recorded and analyzed offline to identify characteristics of the user's learning process. According to an embodiment, the remote processing and storage module 150 can receive data captured by the systems of the interactive environment system 170 and analyze the data received from the interactive environment system 170 to assess the state of the user during the task or tasks. For example, in a marksmanship training environment, the interactive environment system 170 can include either a real gun or simulated gun to which one or more sensors has been affixed. For example, the gun or simulated gun can have a pressure sensor affixed to the trigger to sense how much pressure a user has applied to the guns trigger. Other types of sensors can also be included, such as an accelerometer for sensing the position of the gun and/or how steady the user is holding the gun. The interactive environment system 170 in the marksmanship training environment can also include one or more targets. The gun can include live ammunition in some embodiments for firing at real targets (e.g., at a gun range) or blank or simulated ammunition can be used. For example, a laser or other alternatives to live ammunition can be used to simulate firing at a target with live ammunition.

In another example, the interactive environment system 170 can comprise a simulated golf environment where the user can be displayed a simulation of a golf course (e.g., projected on a screen or using a virtual reality goggles). The user can be provided a golf club that includes sensors, such as an accelerometer for sensing the characteristics of the user's swing. In yet another embodiment, the interactive environment system 170 can include real world deployments of the portable training module or modules 100 into real world training environment, such as a gun range, a golf course, or a sports field, where the user can interact with the training environment and sensors, cameras, etc. deployed in the environment can be used to capture performance data and provide the performance data to the remote processing and storage module 150, which can also be deployed at the real-world location (e.g., as a laptop computer or other mobile device). Alternatively, the interactive environment system 170 can capture data that can be later transmitted or copied to the remote processing and storage module 150.

Rules module 160 includes a set of rules and indices that can be customized to or personalized to suit the needs of a particular task or user. The rules module 160 can be configured to receive data from remote processing and storage module 150 and to configure the rules accordingly. The rules can be configured to customize the training experience for a particular user. For example, an instructor can provide qualitative feedback regarding the user's learning progress using the qualitative assessment module 175. This feedback can then be used by remote processing and storage module 150 to configure the rules to intensify, terminate, or otherwise modify the training process. For example, the rules can be used in conjunction with the expert metrics information to select the set of which of the one or more goals states a user should reach in order to complete a training exercise. The rules can also be used to define the types of feedback to be provided to a user based on the user's current state and the one or more goal states associated with the selected training profile. The feedback can be selected that can help steer the user toward the one or more goal states associated with the training profile.

According to an embodiment, the system for accelerating skill learning can be configured to provide automated tutorials with neurocognitive profiling. In some embodiments, event-related potentials (ERPs) can be employed to explore multiple levels of information processing. For example, locked data extraction and analysis employing well know techniques such as power spectral analysis, wavelet analysis, and/or other techniques.

According to an embodiment, the system can also be configured to introduce stressful real world conditions into a training program. For example, first person shooter games can be introduced in marksmanship training to encourage a combat mindset.

The system for accelerated learning and the methods of use described herein can be used to reduce the number of instructors required to trains a user for a particular task. According to an embodiment, the system can provide an interactive learning environment, where the instructor can provide qualitative and/or quantitative performance assessments. The instructor can provide pre-training and/or in-training triage and/or intervention to assist the learning process. According to an embodiment, the qualitative assessment module 175 is configured to provide a user interface for the instructor to provide qualitative and/or quantitative assessment information to the user. In an embodiment, the user interface comprises a web page or a set of web pages that allow the instructor to enter assessment information and/or view user performance data collected by the system. According to an embodiment, the qualitative assessment module 175 can be implemented on the remote processing and storage module 150. In other embodiments, the qualitative assessment module 175 can be implemented on a remote computer system (not shown) that provides a user interface that allows an instructor to provide feedback and the remote computer system is in communication with the remote processing and storage module 150 via a wired or wireless network connections, such as via the Internet.

Stored profiles module 165 can be configured to extract the basis of expert performance that is common to at least 80% of the population for whom performance data has been recorded. The recorded performance information can be recorded using various types of sensors that record neurophysiological measurements and multi-sensory feedback from experts performing a task to be trained. Examples of some of the types of sensors that can be used are described above. The recorded performance information can then be analyzed using the stored profiles module 165 and/or the remote processing and storage module 175 to generate profiles that can be used to assess the performance of a user using the system to accelerate the learning of a task. The information extracted by the stored profiles module 165 can form the basis for the expert metrics stored in the expert metrics data store 115.

Figure 2:
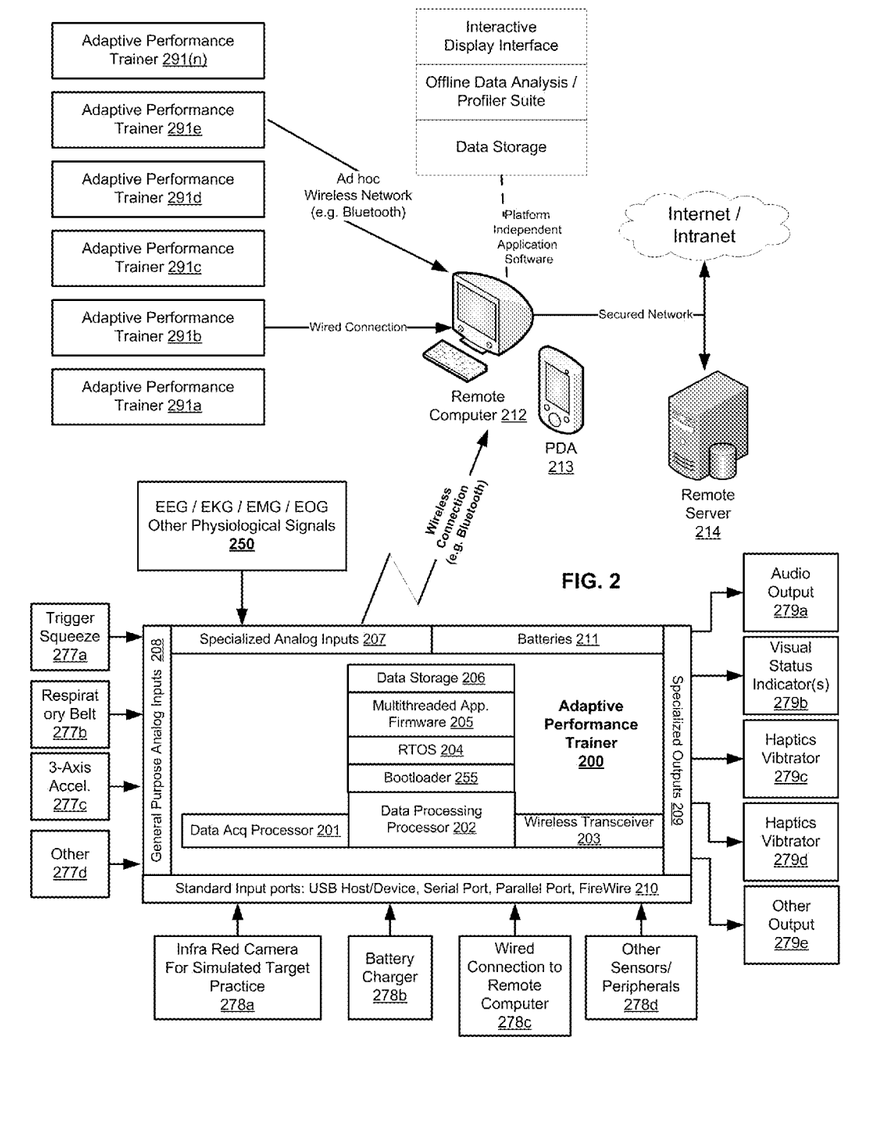
FIG. 2 illustrates an exemplary embodiment of an adaptive performance training system that can be used to implement the system for accelerated learning illustrated in FIG. 1 according to an embodiment.

FIG. 2 illustrates an exemplary embodiment of an adaptive performance training system that can be used to implement the system for accelerated learning illustrated in FIG. 1. In the embodiment illustrated in FIG. 2, peripherals and accessories for use in rile marksmanship training are described. However, this is merely one embodiment of the system for accelerating training. In other embodiments, different combinations of sensors can peripherals can be used, depending upon the type of training to be performed. The basic architecture of the system is versatile and modular, and can be easily reconfigured for a variety of tasks and deployed in various environments for learning selected tasks.

The system illustrated in FIG. 2 includes an adaptive performance trainer (APT) 201. The adaptive performance trainer 200 corresponds to the portable training module 100 illustrated in FIG. 1, and can interact with the interactive training environment (e.g., interactive environment system 170) with which the user interacts during a training session. According to an embodiment, the adaptive performance trainer is a rechargeable, battery powered device that can be reconfigured for use in various training environments. The adaptive performance trainer 200 can be used to implement the portable training module 100 illustrated in FIG. 1 according to an embodiment. The embodiment of the adaptive performance trainer 200 illustrated in FIG. 2 comprises a dual-core architecture. In this embodiment, tasks related to data acquisition and tasks related to data processing are distributed among two different processors. Data acquisition processor 201 can be configured collect analog and digital input data, and one or more data processing processors 202 can be configured to execute complex, multi-threaded real-time algorithms for data processing. According to an embodiment, raw data collected by the data acquisition processor 201 and/or outputs from the data processing algorithms can be stored in the non-volatile memory 206 for offline processing. According to an embodiment, memory 206 can be implemented using a flash memory, while in other embodiments, other types of persistent computer readable and writeable memory can be used. According to alternative embodiments, a single processor or more than two processors can be used.

The adaptive performance trainer 200 includes a bootloader 255 that is configured to boot up or initialize the real time operating system 204 of the adaptive performance trainer 200. The real-time operating system 204 is configured to execute multithreaded application firmware 205. According to some embodiments, the real-time operating system 204 can also be used to execute multithreaded software stored in a computer-readable medium, such as data storage 206.

Data storage 206 can also be used to store expert metrics information to implement the expert metrics data store 115 that has been provided from remote computer system 212, mobile device 213, and/or remote server 214.

In an embodiment, the data acquisition processor 201, real time operating system 204, the multithreaded application firmware 205, memory 206, and data and/or executable program code stored in memory 206 as well as general purpose analog inputs 208, specialized analog input ports 207, and standard input ports 210 can be used to implement monitor module 110 illustrated in FIG. 1.

In an embodiment, the one or more data processing processors 202, real time operating system 204, and the multithreaded application firmware 205, memory 206, and data and/or executable program code stored memory 206 can be used to expertise profiler module 120 illustrated in FIG. 1.

In an embodiment, the one or more data processing processors 202, real time operating system 204, the multithreaded application firmware 205, and memory 206 can be used to implement the expertise profiler module 120 illustrated in FIG. 1. In an embodiment, the data acquisition processor 201, real time operating system 204, the multithreaded application firmware 205, memory 206, and data and/or executable program code stored in memory 206 as well as specialized output ports 209 can be used to implement real-time feedback generator module 130 illustrated in FIG. 1.

The adaptive performance trainer 200 can include a variety of input and output ports for interfacing with an extensive array of sensors and peripherals. FIG. 2 illustrates one possible configuration. According to an embodiment, the sensors and peripherals can include proprietary and third-party sensors/peripherals and for providing multi-modality feedbacks.

Specialized analog input ports 207 can be used to collect analog physiological signals 255 including electroencephalogram (EEG), electrocardiogram (EKG), electrooculogram (EOG), electromyogram (EMG), or other physiological signals, or a combination thereof. According to an embodiment, the specialized analog input ports 207 can include specialized hardware filters and amplifications blocks that to capture these signals with minimal distortion and artifacts.

General purpose analog inputs 208 provide an interface for receiving data from other types of conventional or unconventional sensors or transducers with analog data output. According to an embodiment, the general purpose analog inputs 208 can include software programmable filters and amplifiers for conditioning and adapting the analog data received from the sensors or transducers to required input specifications. For example, in the in rifle marksmanship training embodiment illustrated in FIG. 2, the sensors interface with general purpose analog inputs 208 include a pressure-sensitive resistor for trigger control 277a, respiratory belt transducer 277b for learning breath control, a multi-axis accelerometer 277c to sense body movement arc, and/or other sensors 277d providing an analog data output. The general purpose analog inputs 208 can also be used to communicate data to and/from the interactive environment system 170.

Standard input ports 210 provide an interface for peripherals communicating on standard protocols. For example, embodiments can include input ports for USB host/device, serial-port, parallel-port, FireWire, and/or other types of input port. According to an embodiment, standard headers can be provided to support protocols, such as Inter-Integrated circuit (I2C), System Packet Interface (SPI), Content Addressable Network (CAN), to interface high speed peripherals. The standard input ports 210 can also be used to communicate data to and/from the interactive environment system 170.

Some typical peripherals that can be used for marksmanship training include an infrared (IR) camera 278a for capturing strikes on a simulated target using a laser used for indoor dry-fire training, specialized outputs from weapons, other peripherals, or a combination thereof. These peripherals can be part of the interactive environment 170 with which the user interacts during a training session. The standard input ports 210 can also be configured interface with a remote computer system via a wired connection 278c to download trend data. The standard input ports can also be configured to a battery charger 278b for recharging battery 211. According to an embodiment, software support can be provided for newly interface peripherals by loading a corresponding driver into the real-time operating system 204 of the adaptive performance trainer 200. According to an embodiment, battery 211 can comprise a rechargeable lithium polymer battery or other type of rechargeable battery. According to alternative embodiments, the battery 211 may comprise one or more non-rechargeable batteries that can be removed from the adaptive performance trainer 200 and replaced.

According to an embodiment, the adaptive performance trainer 200 can provide multimodality feedback outputs through a variety of output ports 209. According to an embodiment, the specialized outputs ports 209 can be used to output control signals to various types of feedback devices that can be used to implement at least part of the interactive environment (e.g. interactive environment system 170 of FIG. 1) in which the user is immersed during training. For example, for marksmanship training, audio output 279a for connecting headphones or speakers that can be used to provide frequency or pulse width modulated outputs proportional to an input parameter and/or audio commands to guide the user during the training, visual status indicators 279b such as light emitting diodes (LEDs) or a mini liquid crystal display (LCD), haptics feedback modules 279c and 279d, such as multiple shaft-less vibration motors for haptics feedback, and other output devices 279e.

According to an embodiment, adaptive performance trainer 200 can also include a wireless transceiver to connect to a remote computer station, such as a personal computer system 212 or a mobile device 213, such as a personal digital assistant, mobile phone, or similar device. According to an embodiment, the wireless transceiver can be configured to support one or more well-known protocols, such as Bluetooth to connect to the remote computer system 212 or the mobile device 213.

According to an embodiment, the data transmitted from the adaptive performance trainer 200 to the remote computer system 212 or mobile device 213 can be stored in a retrievable database format in either in a data store on the remote computer system 212 or the mobile device 213. The data in the data store can be used for offline analysis of the performance and/or to make recommendations and to provide feedback to the user during a training session. According to some embodiment, the remote computer system 212 or the mobile device 213 can include an interactive user interface that can be used to run additional tests, to educate the user prior to the training session, to provide additional feedback during or after the test, or a combination thereof. For example, in rifle marksmanship training, the interactive training environment can include a simulated laser target can be provided for indoor dry firing practice. According to an embodiment, the user can interact with the system for accelerating skill learning through various types of interactions and interfaces, including but not limited to, key presses, mouse clicks, a degree of pressure on a joysticks or other types of pressure-sensitive equipment or computer interface, or a combination thereof.

According to an embodiment, the remote computer station can be communicatively coupled to a remote server 214 via a secure network connection. According to an embodiment, the remote server 114 can provide a password-protected web interface for monitoring data and the status of the training both during and after the training process.

In an embodiment, the remote computer system 212, the mobile device 213, the remote server 214, or a combination thereof can be used to implement the remove processing and storage module 150, the rules module 160, the stored profiles module 165, and the qualitative assessment module 175 illustrated in FIG. 1.

In an embodiment, the adaptive performance trainer 200 can be configured to shape the psychophysiological state of user toward a peak performance state characteristic of an expert in the task to be performed just prior to a particular task is to be performed. For example, the adaptive performance trainer 200 can be configured to shape the user toward a peak performance state characteristic of an expert marksman several seconds before the use is to take a shot. In another embodiment, the adaptive performance trainer 200 can be configured to shape the user toward a peak performance state characteristic of an expert golfer before the user is about to hit a ball. In yet another embodiment, the adaptive performance trainer 200 can be configured to shape the user toward a peak performance state characteristic of an expert basketball player before the user is about to shoot a free throw. In an embodiment, the peak performance state includes an increase in EEG theta (4-7 Hz) and alpha (8-12 Hz) power, low EEG engagement levels, and high EEG workload levels.

In an embodiment, other pre-shot physiological indicators of expertise include a local decrease in heart rate, low sympathetic activation (a measure of stress and anxiety), breath control (shot taken during the natural respiratory pause), and trigger control (slow and steady trigger pull). According to an embodiment, the accelerated training system is configured to incorporate various profiles of expertise (empirical or theoretical) that are stored as model goal states and then used to accelerate the progression from novice-to-expert based on automated inferences from the neurophysiological measurements. As described above, stored profiles module 165 can be used to store the expert profiles. According to an embodiment, the system integrates real-time EEG metrics (Alpha and Theta) and heart rate to provide the user with automated feedback on their psychophysiological state as compared to that of experts in the pre-shot period. For example, if the user is on the golf course or shooting range, haptic feedback can be delivered to the user via two small vibratory sensors placed on the back of the neck, which indicate to the user that he or she is in an ideal state to take a shot.

In an alternative embodiment, feedback training can be provided that is based on previously established psychophysiological goal profiles, such as breathing, heart rate and EEG alpha control for relaxation training and anxiety reduction. In this embodiment, the accelerated learning system can use the same key functionalities: 1) acquisition and processing of EKG, respiration & 4-channel EEG, 2) real-time feedback of heartbeat via haptics and audio, 3) real-time feedback of alpha-state via haptics and audio and 4) wireless transmission of EKG & EEG to remote computer via Bluetooth protocol or other wireless protocol for display and offline analysis to assist the user in achieving a specific state.

According to an embodiment, the adaptive performance trainer 200 can assist in shaping novice users into an expert pre-shot peak performance state. In an embodiment, the training system employs visual, audio and haptic feedback alone, or in combination, to help users train to control their physiology. According to an embodiment, a haptic vibratory unit can be placed on each of the user's shoulders, such as haptics vibrators 279c and 279d to help shape the state of the user. For example, in the marksman training example, the haptics vibratory units can be configured to "tap" the user on the shoulders in a pace that replicates the actual heartbeat of the participant making them more aware of their heart rate deceleration that is associated with exhalation and that ideally precedes the trigger pull. When alpha is at or below baseline level, both haptic units vibrate. As alpha increases above normal, one haptic unit stops vibrating and when alpha reaches an ideal state, both haptic units stop vibrating, thus alerting the user that he or she has reached an ideal shooting state. The use of haptics to provide both alpha and heart rate feedback simplifies the stream of information that is provided to user. As a result, maximal feedback can be provided to the user to guide the user toward a greater awareness and control over his or her physiology as seen in experts without overloading the user with information.

Transition from novice to expert requires practice. Repetition alone however, does not ensure success, and repetition of poor technique can lead to negative training, which can result in performance deficiencies and/or stress injuries. Recent investigations have suggested that motor skill learning may be dependent upon the availability of cognitive resources, including attention and working memory, and that the speed and efficiency of learning may be affected by either state or trait differences in these cognitive capacities.

The adaptive performance trainer 200 can directly assess these states or trait differences using knowledge about EEG signatures as well as an array of other physiological metrics that change during stages of learning. The adaptive performance trainer 200 can be configured to provide continuous psychophysiological monitoring and feedback (visual, auditory, and/or haptic feedback) on relevant changes in these measures to the user in real time. One advantage of the adaptive performance trainer over conventional training techniques is the ability of the adaptive performance trainer to first characterize the psychophysiological profile of expertise, and then provide individualized tailored feedback to the user to shape the user into the psychophysiological state of an expert. The APT design offers multiple options for training including: sensor inputs (EEG, EKG, respiration, eye tracking), algorithms for deriving state changes (based on single or multiple sensor inputs, designed for shaping to an expert model) and feedback delivery (visual, audio, haptic or multimodality). Training can be customized to meet the needs of the investigators or the trainees. The training protocols can then be streamlined and optimized for field deployability.

FIG. 2 also includes adaptive performance trainers 291a-291n, which can be of a similar configuration as adaptive performance trainer 200. According to some embodiments, for multi-user and team activities, multiple adaptive performance trainers 291a-291n can be configured to communicate in an ad-hoc wireless network, where each of the adaptive performance trainers can be interface to the remote computer station which can be configured act as a master device for receiving data from the adaptive performance trainers 291a-291n and for sending instructions to the adaptive performance trainers 291a-291n to coordinate the training program. Each of the adaptive performance trainers 291a-291n can be configured to provide individualized analysis of data collected from their respective users and provide individualize feedback to each of the users. In an embodiment, a plurality of adaptive performance trainers can be used in with an interactive environment system such as interactive environment system 170 that is deployed at a team sports facility, such as a soccer field or baseball field, where sensors have been deployed to capture performance information for users of the system for accelerating learning.

Figure 3:
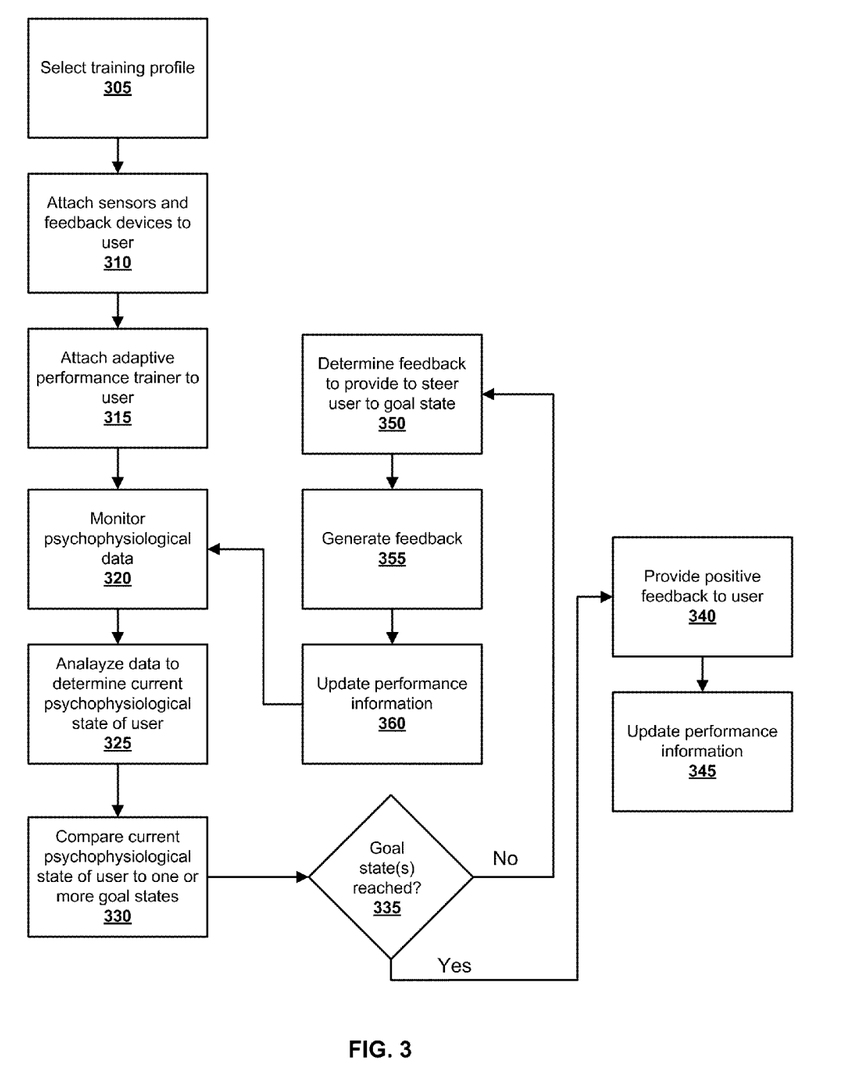
FIG. 3 is a flow diagram of a method for accelerating learning using the systems illustrated in FIGS. 1 and 2 according to an embodiment.

FIG. 3 is a flow diagram of a method for accelerating learning using the systems illustrated in FIGS. 1 and 2 according to an embodiment. The steps referenced in FIG. 3 make reference to the adaptive performance trainer 200 of FIG. 2, but as described above, the adaptive performance trainer is merely on possible embodiment of the portable training module 100 illustrated in FIG. 1. Therefore, the steps of the method describe in FIG. 3 equally apply to the various components and modules described in FIG. 1.

The method can be used to facilitate accelerated learning of one more tasks. For example, the method can be used to steer the user of the adaptive performance trainer toward one or more psychophysiological goal states associated with expert-level performance of a task to be learned. In an embodiment, the method can be used to assist in the adaptive performance training of the user to in a sport, such golf, basketball, shooting, and/or other sports where the performance of the user can be monitored and the user steered toward one or more psychophysiological goal states associated with expert-level performance of one or more tasks related to the sport, such as shooting a ball, shooting a gun, or swinging a golf club.

A training profile to be used in the training session is selected (step 305). A training profile can be associated with a particular task or activity to be performed. For example, an expert profile can be created for marksmanship training, golf, or other activities where a user can benefit from the adaptive learning techniques described herein. As described above, expert profiles for various tasks or activities can be created by monitoring the neurological and psychophysiological state of experts performing a task to be learned by others. For example, a golf professional can be monitored while performing a task, such as swinging a club to collect information related to the neurological and psychophysiological state of the golf professional before and during the swing, and the data collected can be analyzed to create an expert profile for accelerated golf instruction. In another example, an expert marksman can be monitored while performing tasks related to marksmanship, such as lining up for shot and shooting a gun, and the data collected can be analyzed to create an expert profile for accelerated marksmanship training. Experts in other types of activities can also be monitored and the collected data analyzed to create expert profiles for these activities. The expert profile can include one or more goal states, neurological and/or psychophysiological states that toward which the adaptive training.

Once a training profile has been selected, various sensors for collecting neurological and psychophysiological data are attached to the user as well as various feedback devices for providing feedback that can help steer the user toward the one or more goal states. For example, embodiments can include sensors for EEG, EKG, EMG, EOG, a respiratory belt for measuring respiration, accelerometers for measuring body position, and/or other types of sensors for monitoring the neurological and psychophysiological state of the user. Various types of feedback devices can also be attached to the user. For example, in an embodiment a set of headphones can be used to provide audio output to the user, and/or a set of haptic vibrators can placed on the user to provide tactile feedback. For example, in marksmanship training, a haptic vibrator can be place on each should of the user in order to provide feedback to the user as the user performs the task to be learned. In some embodiments, feedback devices can also be incorporated into the adaptive performance trainer module. For example, in an embodiment, the adaptive performance trainer module can include a speaker for providing audio feedback and/or a haptic vibrator for providing tactile feedback to the user.

Once the sensors have been attached to the user, the adaptive performance trainer 200 can be attached to the user (step 315). According to some embodiments, the adaptive performance trainer 200 can be help in place by a strap or belt. In some embodiments, the position of the adaptive performance trainer on the body of the user is determined at least in part on the type of training to be performed.

Once the sensors and the adaptive performance trainer have been put in place on the user, the adaptive performance trainer can begin monitoring neurological and/or psychophysiological data from the various sensors and/or from other external data sources, such as an infrared camera 278a and/or other sensors and peripherals 278d (step 320). The infrared camera 278a and/or other sensors and peripherals 278d can be part of the interactive environment system 170.

The data received from the sensors and/or other inputs can then be analyzed to determine a current psychophysiological state of the user (step 325). The current psychophysiological state of the user can then be compared with the one or more goal states associated with the selected training profile (step 330). A determination can then be made whether the one or more of the goals associated with the selected training profile have been reached (step 335). According to some embodiments, the training profile might specify which of the one or more goals must be met in order to satisfy the training requirements associated with the profile. For example, different profiles might be developed for different steps in the training process, such as beginner, intermediate, and advanced profiles, that progressively require that the user reach more of the goal states associated with the training profile.

If the user has reached a state that satisfies the requirements of the training profile, the user can be provided positive feedback (step 340), and performance information used to track the progress of the user can be updated (step 345). This performance information can later be used to generate detailed reports regarding the progress of the user in learning the task. For example, in marksmanship training, a training profile might require the user to maintain a specified body position, a certain respiration pattern, and demonstrate a certain level of focus just prior to pulling the trigger. If these goal states are met, the user might be provided haptic, optical, auditory, or other feedback indicating that the user has reached the desired state. An instructor can also view this performance information to provide qualitative and/or quantitative feedback to the user.

Alternatively, if the user has not yet reached a state that satisfies the requirements of the training profile, the adaptive performance trainer can determine feedback to provide to the user to steer the user toward a desired state (step 350). Once the feedback has been determined, the adaptive performance trainer can output signals to one or more feedback devices to cause the devices to generate feedback. For example, an auditory signal, such as a tone or voice instructions can be generated, visual signals, such as lights or a display can be updated to provide feedback, and/or haptic devices might be activated to provide tactile feedback. For example, a haptic sensor might be activated to indicate that the user should adjust the rate of respiration or adjust the position of his or her arm. Various combinations of feedback devices and combinations of feedback signals can be provided based on the type of training being undertaken. Performance information used to track the progress of the user can be updated (step 360) to reflect the user's neurological and physiological state before and/or after providing the feedback to track the user's progress toward learning the task and reaching the desired goal states associated with expert performance of the task. Once the feedback has been provided to the user, the adaptive performance trainer can continue monitoring the user to determine whether the feedback has helped to the user to move toward the one or more goal states.

One skilled in the art will recognize that FIG. 3 illustrates one possible method accelerating learning and that in alternative embodiment the steps can be combined in a different order and/or additional steps can be added. For example, the adaptive performance trainer can be attached to the user before the sensors are attached to the user in some embodiments. Furthermore, the training profile can be selected after the sensors and the adaptive performance trainer have been attached to the user.

Various illustrative implementations of the present invention have been described. However, one of ordinary skill in the art will see that additional implementations are also possible and within the scope of the present invention. Those of skill in the art will appreciate that the various illustrative modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor or controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in computer or controller accessible on computer-readable storage media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

What is claimed is:

1. A system for accelerating learning of a task using real-time data acquisition and analysis of real-time psychophysiological signals obtained from a user, the system comprising:
   one or more hardware processors;
   a monitoring module configured to, when executed by the one or more hardware processors, continuously monitor psychophysiological signal data collected from a plurality of sensors attached to a user during a pre-shot period of the task to be learned;
   an expertise profiler module configured to
      analyze the psychophysiological signal data to generate a current psychophysiological state of the user by computing one or more power spectral density indices from electroencephalographic activity of the user and converting the one or more power spectral density indices into one or more probabilities that the user's level of mental effort and engagement belongs to one of a plurality of classes using a discriminant function,
      compare the current psychophysiological state of the user to one or more goal states associated with expert performance of the task to be learned, and
      generate a set of control signals based on difference between the current psychophysiological state of the user to one or more goal states; and
   a real-time feedback generator configured to, when executed by the one or more hardware processors, during the pre-shot period,
      receive the control signals from the expertise profiler module, and
      generate at least one multimodality feedback signal to provide feedback to guide the user toward the one or more goal states, wherein the multimodality feedback signal is based on the control signals received from the expertise profiler module, wherein the feedback comprises a tactile indication to the user of the user's current psychophysiological state at a pace that replicates the user's heartbeat, and wherein the tactile indication of the user's current psychophysiological state decreases as the user's current psychophysiological state approaches an ideal shooting state for the task to be learned.

2. The system of claim 1 wherein the monitoring module is configured to continue to monitor the psychophysiological signal data after the feedback has been delivered to the user; and wherein the system is configured to determine whether the feedback delivered to the user has helped the user to reach the one or more goal states.

3. The system of claim 1 wherein the monitoring module is further configured to monitor additional parameters of task performance, including monitoring user interaction with one or more interfaces for capturing user interactions with the system.

4. The system of claim 1 wherein the system further comprises one or more feedback devices, and wherein the multimodality feedback signal activates the one or more feedback devices.

5. The system of claim 4 wherein the one or more feedback devices includes a video display.

6. The system of claim 4 wherein the one or more feedback devices includes an audio output device.

7. The system of claim 4 wherein the one or more feedback devices includes a haptic vibrator.

8. The system of claim 4 wherein the system is configured to be worn on the user's body.

9. The system of claim 1 further comprising a wireless data interface configured to transmit psychophysiological signal data collected by the monitoring module to a remote computer station.

10. The system of claim 9 wherein the remote computer station is configured to receive psychophysiological signal data from the wireless data interface, perform offline analysis of the psychophysiological signal data, and generate performance feedback to assist the user in improving performance of the task.

11. The system of claim 9 wherein the remote computer station includes an interface for receiving feedback data from an instructor, wherein the system is configured to receive the feedback data from the system via the wireless interface, and wherein the system is configured to adjust the one or more goal states used by the expertise profiler module according to the feedback data.

12. The system of claim 1 wherein the psychophysiological signal data includes one or more of electroencephalograph (EEG) data, electrocardiograph (EKG) data, electromyography (EMG) data, respiration data, muscle tone, blood pressure, body temperature, blood flow, galvanic skin reaction, and movement data.

13. The system of claim 1, wherein the psychophysiological signal data comprises electroencephalographic activity data, and wherein computing the one or more power spectral density indices comprises:
determining one or more event-related potentials from the psychophysiological signal data, wherein each of the one or more event-related potentials represents a response to at least one task-related stimulus; and
computing the one or more power spectral density indices on one or more segments of the electroencephalographic activity data, wherein each of the one or more segments of the electroencephalographic activity data corresponds to at least one of the one or more event-related potentials centered to either a task-related stimulus, a response to a task-related stimulus, or a physiological event.

14. The system of claim 1, wherein the one or more goal states are derived from physiological measurements previously acquired from experts performing the task to be learned.

15. The system of claim 1, wherein generating the set of control signals comprises selecting one or more types of feedback from a plurality of available types of feedback based on the difference between the current psychophysiological state of the user to the one or more goal states, and generating the set of control signals for the selected one or more types of feedback.

16. The system of claim 1, wherein the tactile indication of the user's current psychophysiological state decreases such that it stops when the user's current psychophysiological state matches the ideal shooting state.

17. The system of claim 1, wherein the tactile indication of the user's current psychophysiological state decreases by:
providing a first amount of haptic feedback when an alpha level of the user is at or below a baseline level; and,
subsequently, providing at least a second amount of haptic feedback when the alpha level of the user is above the baseline level;
wherein the second amount of haptic feedback is less than the first amount of haptic feedback.

18. A method for accelerating learning of a task using real-time data acquisition and analysis of real-time psychophysiological signals obtained from a user using an adaptive portable training device worn by the user, the method comprising:
continuously monitoring at the portable training device psychophysiological signal data from a plurality of sensors attached to a user during a pre-shot period of the task to be learned; and,
during the pre-shot period,
analyzing at the portable training device the psychophysiological signal data to generate a current psychophysiological state of the user by computing one or more power spectral density indices from electroencephalographic activity of the user and converting the one or more power spectral density indices into one or more probabilities that the user's level of mental effort and engagement belongs to one of a plurality of classes using a discriminant function,
comparing at the portable training device the current psychophysiological state to one or more goal states associated with expert performance of the task to be learned,
determining at the portable training device multimodality feedback to be provide to the user based on the comparison of the current psychophysiological state of the user to the one or more goal states, and
delivering from the portable training device the multimodality feedback to the user in real-time to guide the user toward the one or more goal states, wherein the multimodality feedback delivered to the user is based on the control signals received from the expertise profiler module, and wherein the multimodality feedback comprises a tactile indication to the user of the user's current psychophysiological state at a pace that replicates the user's heartbeat, and wherein the tactile indication of the user's current psychophysiological state decreases as the user's current psychophysiological state approaches an ideal shooting state for the task to be learned.

19. The method of claim 18 further comprising:
continuing to monitor the psychophysiological signal data from a plurality of sensors after the feedback has been delivered to the user; and
determining whether the feedback delivered to the user has helped the user to reach the one or more goal states.

20. The method of claim 18 wherein the psychophysiological signal data includes one or more of electroencephalograph (EEG) data, electrocardiograph (EKG) data, electromyography (EMG) data, respiration data, muscle tone, blood pressure, body temperature, blood flow, galvanic skin reaction, and movement data.

21. The method of claim 18 wherein monitoring psychophysiological signal data from a plurality of sensors attached to a user further comprises:
 monitoring additional parameters of task performance, including monitoring user interaction with one more interfaces for capturing user interactions with the system.

22. The method of claim 18 wherein delivering the multimodality feedback to the user to guide the user toward the one or more goal states further comprises:
 generating a control signal for one or more feedback devices based on the multimodality feedback to be provided to the user.

23. The method of claim 22 wherein the one or more feedback devices includes a video display.

24. The method of claim 22 wherein the one or more feedback devices includes an audio output device.

25. The method of claim 22 wherein the one or more feedback devices includes a haptic vibrator.

26. The method of claim 22 wherein the adaptive performance trainer can be worn on the user's body.

27. The method of claim 18 further comprising:
 receiving psychophysiological signal data at a remote computer system from the adaptive performance trainer via a wireless data interface;
 performing offline analysis of the psychophysiological signal data; and
 generating performance feedback data to assist the user in improving performance of the task.

28. The method of claim 18 further comprising:
 receiving psychophysiological signal data at a remote computer system from the adaptive performance trainer via a wireless data interface; and
 receiving feedback data from an instructor at the remote computer system.

29. The method of claim 28 further comprising:
 receiving at the portable training device the feedback data from the remote computer system; and
 adjusting the one or more goal states used to assess progress of the user based on the feedback data.

30. The method of claim 18 wherein the accelerating learning of the task includes at least one of improving performance on the task, decreasing an amount of time to learn the task, improving the user's retention of the task once learned, and improving the user's ability to change from a first psychophysiological state to a second psychophysiological state during a training session.

31. The method of claim 18, wherein the psychophysiological signal data comprises electroencephalographic activity data, and wherein computing the one or more power spectral density indices comprises:
 determining one or more event-related potentials from the psychophysiological signal data, wherein each of the one or more event-related potentials represents a response to at least one task-related stimulus; and
 computing the one or more power spectral density indices on one or more segments of the electroencephalographic activity data, wherein each of the one or more segments of the electroencephalographic activity data corresponds to at least one of the one or more event-related potentials centered to either a task-related stimulus, a response to a task-related stimulus, or a physiological event.

32. The method of claim 18, wherein the one or more goal states are derived from physiological measurements previously acquired from experts performing the task to be learned.

* * * * *